United States Patent
Parhi et al.

(10) Patent No.: US 7,153,982 B2
(45) Date of Patent: Dec. 26, 2006

(54) METHOD FOR THE PRODUCTION OF A PHENOLIC SUBSTANCE FROM WOOD

(75) Inventors: Seppo Parhi, Oulu (FI); Mervi Puska, Turku (FI); Arja Kalapudas, Oulu (FI); Helena Korte, Turku (FI); Petri Hukka, Oulu (FI)

(73) Assignee: Hormos Medical Corporation, Turku (FI)

( * ) Notice: Subject to any disclaimer, the term of this patent is extended or adjusted under 35 U.S.C. 154(b) by 156 days.

(21) Appl. No.: 10/493,031

(22) PCT Filed: Nov. 15, 2002

(86) PCT No.: PCT/FI02/00905

§ 371 (c)(1),
(2), (4) Date: Apr. 19, 2004

(87) PCT Pub. No.: WO03/044004

PCT Pub. Date: May 30, 2003

(65) Prior Publication Data

US 2004/0267029 A1    Dec. 30, 2004

(30) Foreign Application Priority Data

Nov. 23, 2001 (FI) .................................. 20012290

(51) Int. Cl.
*C07D 305/12* (2006.01)
(52) U.S. Cl. ...................................... 549/323; 549/323
(58) Field of Classification Search ................. 549/323
See application file for complete search history.

(56) References Cited

U.S. PATENT DOCUMENTS 5,229,419 A * 7/1993 McLaughlin et al. ....... 514/473

FOREIGN PATENT DOCUMENTS

GB         2 063 856     6/1981
WO         WO 00/59946   10/2000

OTHER PUBLICATIONS

Freudenberg et al., "Die Lignane Des Fichtenholzes"0- Chem. Ber. 2857-69 (1957).
Ekman, "Analysis of Lignans in Norway Spruce by Combined Gas Chromatography—Mass Spectrometry", 30 *Holzforschung*79-85 (1976).
★Modonova et al., "Lignan Compounds of Siberian Sprice Wood (Picea Obovata)," Khim. Ispol'z. Lignina 73-86 (1974) abstracted in STN International, File CAPLUS, Accession No. 1975:141811 (Abstract Only).
★Kuridze et al., "Spectrophotometric Determination of Lignans in Oakwood and Brandy," 7 Izvestiya Akademii Nauk Gruzinsko: SSR, Serija Khimicheskaya 213-23 abstracted in STN International, File CAPLUS, Accession No. 1982:102372 (Abstract Only).

* cited by examiner

*Primary Examiner*—Thomas McKenzie
*Assistant Examiner*—Raymond Covington
(74) *Attorney, Agent, or Firm*—James C. Lydon

(57) ABSTRACT

A method for the production of hydroxymatairesinol or a hydroxymatairesinol complex from wood, including the steps of a) extracting finely divided wood material with a polar solvent, b) optionally concentrating the extract by separating at least part of the solvent, c) adding to the extract an agent able to form a complex with hydroxymatairesinol, d) precipitating the hydroxymatairesinol complex, and optionally e) releasing the hydroxymatairesinol from the complex.

11 Claims, No Drawings

METHOD FOR THE PRODUCTION OF A PHENOLIC SUBSTANCE FROM WOOD

This application is a U.S. National Stage of International application PCT/FI02/00905, filed Nov. 15, 2002.

FIELD OF THE INVENTION

This invention relates to a method for recovery of hydroxymatairesinol or a hydroxymatairesinol complex from wood material, particularly to a method for large scale production of hydroxymatairesinol or a complex thereof from wood.

BACKGROUND OF THE INVENTION

The publications and other materials used herein to illuminate the background of the invention, and in particular, cases to provide additional details respecting the practice, are incorporated by reference.

Hydroxymatairesinol (HMR) which has the formula

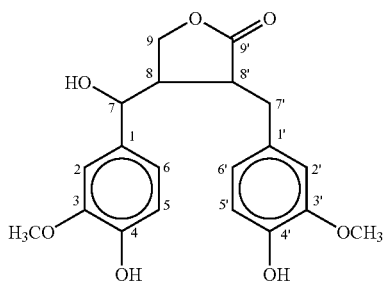

is a lignan, i.e. a class of phenolic substances widely distributed in plants. Hydroxymatairesinol appears as two diastereomers, namely (−) hydroxymatairesinol (also denoted HMR 2 isomer) and (−) allo-hydroxymatairesinol (HMR 1 isomer).

Hydroxymatairesinol has been disclosed to possess valuable therapeutical properties and has been suggested for use in prevention of cancer, certain hormone-dependent diseases and/or cardiovascular diseases, or for increasing the enterolactone level in a person's serum. Hydroxymatairesinol has thus been suggested for use as a food supplement or as a medicament (International patent publication WO 00/59946). It has further been found that the HMR 2 isomer is more biologically active than the HMR 1 isomer.

Considerable amounts of lignans are found in coniferous trees. The type of lignans differs in different species and the amounts of lignans vary in different parts of the trees. The typical lignans in heart wood of spruce (Picea abies) are hydroxymatairesinol (HMR), α-conidendrin, conidendric acid, matairesinol, isolariciresinol, secoisolariciresinol, liovil, picearesinol, lariciresinol and pinoresinol (Ekman 1979). The far most abundant single component of lignans in spruce is hydroxymatairesinol (HMR), about 60 percent of total lignans, which occurs mainly in unconjugated free form. Lignan concentration in thick roots is 2–3 percent. Abundance of lignans occur in the heart wood of branches (5–10 percent) and twists and especially in the knots, where the amount of lignans may be higher than 10 percent (Ekman, 1976 and 1979). These concentrations are about hundred-fold compared to ground flax powder known as lignan-rich material.

It has been suggested to isolate hydroxymatairesinol from compression-wood fiber. These fibers originate from compression wood of stems and knots (oversize chip fraction) and they are known to weaken the quality of paper (Ekman, 1976).

Earlier described methods for the recovery of hydroxymatairesinol from wood:

Ekman 1976 and Ekman 1979 describe a laboratory extraction method for recovering hydroxymatairesinol from ground heartwood of Norway spruce. The wood material was first Soxhlet-extracted with hexane to remove lipophilic components. Then the wood material was re-extracted with a mixture of acetone and water (9:1) to give a mixture of crude lignans. Hydroxymatairesinol was isolated from the mixture by chromatography.

Freudenberg & Knof, 1957, described the extraction of wood meal with acetone and water. The extract was separated into different fractions by formamide, water and ether. The hydroxymatairesinol-rich fraction was separated into the two isomers (amorphous (−) hydroxymatairesinol and crystalline (−) allo-hydroxymatairesinol) either by chloroform and water, or by crystallizing the isomer (−) hydroxymatairesinol potassium acetate adduct by adding alcohol and potassium acetate to the hydroxymatairesinol-rich fraction containing both isomers.

However, no suitable process for large scale recovery of HMR from wood has been described in the literature.

The present invention fulfils a great need for a convenient production method of hydroxymatairesinol in large scale from wood material. The new method has many advantages over previously described methods:

the method comprises only a few steps, in principle only the extraction step and the precipitation (e.g. crystallization) step of the hydroxymatairesinol complex formed the same kind of solvent can be used in both steps solvents accepted by the health authority regulations can be used in both steps there is no need to separate the extract into different fractions before the addition of the complexing agent the complex formed can be used as such as a commercial product the product derived has a purity which is good enough for end use of the product.

SUMMARY OF THE INVENTION

This invention concerns a method for the production of hydroxymatairesinol or a hydroxymatairesinol complex from wood, comprising the steps of a) extracting finely divided wood material with a polar solvent, and b) optionally concentrating the extract by separating at least part of the solvent.

The method is characterized by c) adding to the extract an agent able to form a complex with hydroxymatairesinol, d) precipitating the hydroxymatairesinol complex, and optionally e) releasing the hydroxymatairesinol from the complex.

DETAILED DESCRIPTION OF THE INVENTION

According to a preferable embodiment, the wood material to be used in the extraction step is finely ground spruce wood, preferably derived from oversized chips of spruce wood. Such oversized chips are rich in knotwood, i.e. the parts of the branches that are embedded in the stem and the branches extending outwards from the stem.

The word "complex" means in this text especially a crystallisable, hydroxymatairesinol-rich product such as an adduct of a carboxylate, but it is not restricted hereto.

Although the process in principle can be carried out by adding the complexing agent directly to the non-concentrated extract, i.e. to the solution separated from the wood substance, it is preferable to withdraw at least part of the solvent used in the extraction step, because precipitation, e.g. crystallization, of the complex is adversely affected if the solution is too diluted, and especially if it contains high quantities of water derived e.g. from moist wood material.

The polar solvent to be used in the extraction step can be a single solvent or a mixture of solvents. The polar solvent is preferably an alcohol. Especially when the hydroxymatairesinol recovered is intended for use as food supplement or for medical use it is preferred that the polar solvents to be used in the extraction step as well in the precipitation step are solvents accepted by health authority regulations.

Suitable solvents to be used in the extraction step are, for example, pure ethanol or a mixture of ethanol and ethyl acetate.

If the precipitated hydroxymatairesinol complex is a crystallized adduct of hydroxymatairesinol and a carboxylate, suitable solvents to be used in the crystallization step are, for example, pure ethanol, pure isopropanol, or a mixture of ethanol or isopropyl alcohol with, for example, toluene, acetone or ethyl acetate. According to a preferable embodiment, the same alcohol is used in the extraction step as well as in the crystallization step.

The extraction can be carried out as a batch process or a continuing process where the mixture of wood particles and the solvent are agitated at elevated temperature for a certain period of time. The extraction can also be carried out as a circulation process, where the finely divided wood material is placed in the pressure filter or a filter type apparatus and the pre-heated extraction solvent or mixture of solvents is circulated through filter type apparatus for a certain period of time.

The complexing agent is preferable a carboxylate, such as acetate, propionate or butyrate of an alkali metal, such as potassium or sodium, an earth alkali metal such as calcium, or ammonium. Such carboxylates form crystallisable adducts with hydroxymatairesinol. Especially in case the derived hydroxymatairesinol is intended to be used as food supplement or for medical use, potassium acetate is a preferable complexing agent.

If so desired, the hydroxymatairesinol can be released from the complex by known chemical methods, such as extraction.

The invention will be illuminated by the following non-restrictive Experimental Section.

Experimental Section

Extraction of Hydroxymatairesinol from Wood

EXAMPLE 1

A batch reactor was charged with 200 kg of ground wood material (ground spruce wood derived from oversized chips) and 1200 l of ethanol was added. The mixture was heated to boiling and stirred 1.5–2.5 h. The mixture was cooled to about 55° C. and the ethanol solution was separated from the wood particles by filtration. The extraction of same wood material was repeated with 600 l of ethanol by using same process parameters. After the extraction was completed, the ethanol was separated from wood material, the two ethanol extracts were combined and finally concentrated by distillation.

EXAMPLE 2

According to the circulation method, the extraction was carried out as follows: A pressure filtration apparatus was charged with 65 kg of finely divided wood. About 600 kg of ethanol was charged into the reactor, heated to about 73° C. and the pre-heated ethanol was circulated through the pressure filter for about 12 h. The ethanol solution was transferred in to the storage tank and the extraction process of the same wood material was repeated under the same conditions with another 600 kg of ethanol. The two ethanol extracts were combined and concentrated by distillation.

Preparation of Potassium Acetate Adduct of Hydroxymatairesinol

EXAMPLE 3

Into the glass reactor 3100 g of hydroxymatairesinol-rich extract (loss on drying 60.6%) obtained in the extraction process described in Example 1, 1860 g of ethyl acetate, 290 g of ethanol; 62 g of acetic acid and 78 g of water were charged. The temperature was adjusted to 25° C. and 465 g of potassium acetate was added, mixture was seeded and agitated over night at 25° C. The product was filtered, washed with ethyl acetate and finally dried under vacuum at 50° C. The yield was 287 g (18.6% calculated from the amount of dry substance in the concentrate). The purity of product was 97 area %.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

R. Ekman, "Analysis of lignans in Norway spruce by combined gas chromatography-mass spectrometry", Holzforschung 30, 79–85 (1976).

R. Ekman, "Distribution of lignans in Norway spruce", Acta Acad. Abo, Ser. B, 39:3, 1–6 (1979).

Freudenberg K and Knof L, "Lignanes des Fichtenholzes". Chem. Ber. 90, 2857–69, 1957.

The invention claimed is:

1. Method for the production of hydroxymatairesinol or a hydroxymatairesinol complex from wood, comprising the steps of
   a) extracting finely divided wood material with a polar solvent,
   b) optionally concentrating the extract by separating at least part of the solvent,
   c) adding to the extract an agent able to form a complex with hydroxymatairesinol,
   d) precipitating the hydroxymatairesinol complex, and optionally
   e) releasing the hydroxymatairesinol from the complex, wherein said wood material is spruce wood enriched in knotwood.

2. The method of claim 1, wherein the agent able to form a complex with hydroxymatairesinol is added together with a polar solvent to a concentrated extract obtained in step b).

3. The method of claim 1, wherein the polar solvent used is an alcohol.

4. The method of claim 1, wherein the polar solvent used in the extracting step is pure ethanol or a mixture of ethanol and another solvent.

5. The method of claim 4, wherein said another solvent is ethyl acetate.

6. The method of claim 1, wherein the extraction process is carried out in a pressure filtration apparatus, wherein the polar solvent or solvent mixture is circulated through a layer of wood particles.

7. The method of claim 1, wherein the extract is concentrated by distilling at least part of the solvent off.

8. The method of claim 2, wherein the polar solvent to be added to the extract is pure ethanol; pure isopropyl alcohol; a mixture of ethanol or isopropyl alcohol in combination with another solvent.

9. The method of claim 2, wherein the agent able to form a complex with hydroxymatairesinol is a carboxylate of an alkali metal, an earth alkali or ammonium, wherein the complex formed with hxydroxymatairesinol is crystallized.

10. The method of claim 9, wherein the carboxylate is potassium acetate.

11. The method of claim 8, wherein said another solvent is ethyl acetate or acetone.

* * * * *